United States Patent [19]

Cook et al.

[11] 3,995,051
[45] Nov. 30, 1976

[54] METHODS AND COMPOSITIONS FOR INDUCING RESISTANCE TO BACTERIAL INFECTIONS

[75] Inventors: Elton S. Cook; Akira Fujii, both of Cincinnati, Ohio

[73] Assignee: Stanley Drug Products, Inc., Portland, Oreg.

[22] Filed: July 10, 1975

[21] Appl. No.: 594,577

Related U.S. Application Data

[63] Continuation of Ser. No. 490,700, July 17, 1974, abandoned.

[52] U.S. Cl. .............................. 424/273; 260/309
[51] Int. Cl.² .................................... C07D 233/64
[58] Field of Search ...................... 260/309; 424/273

[56] References Cited
UNITED STATES PATENTS 3,825,560   7/1974   Saito et al. ...................... 260/326.45

Primary Examiner—Henry R. Jiles
Assistant Examiner—C. M. S. Jaisle
Attorney, Agent, or Firm—John G. Schenk

[57] ABSTRACT

A variety of substances are reported which alter host resistance to cocci and bacilli bacterial infections. Nevertheless, because of the extreme difficulty of total eradication, and the frequent reappearance of the same strains, even after their apparently successful elimination, there is a continuing need for drugs for the treatment of coccic infections. Certain guanidinoacylhistidines are effective in inducing resistance to infections due to cocci and bacilli.

12 Claims, No Drawings

METHODS AND COMPOSITIONS FOR INDUCING RESISTANCE TO BACTERIAL INFECTIONS

This is a continuation of application Ser. No. 490,700, filed July 17, 1974, now abandoned.

BACKGROUND OF THE INVENTION

This invention pertains to antimicrobials. In a particular aspect this invention relates to antimicrobials effective in protecting against cocci and bacilli bacterial infections.

Bacteria such as cocci and bacilli are a unique group of organisms embodying within themselves an array of yet unanswered puzzles in biology, both fundamental and experimental. It is recognized that the significance of staphyolococcal infections is not so much in severity, except in a few instances, as in the subleties of the infection due to the unpredictable vagaries of these organisms. The result is the disease continues to be a problem.

Treatment of staphylococcal diseases is complicated by the ability of the organisms to develop resistance. The magnitude of the problem is further amplified by the extreme difficulty of total eradication, and the frequent reappearance of the same strain even after apparently successful elimination. The inability to eliminate the carrier state by any of the currently known methods and the prevalence of the new antibiotic resistant hospital strains have added a new dimension to the frustration situation.

Penicillin G (benzyl penicillin) is still the drug of choice for the treatment of infections caused by susceptible coccic strains. However, numerous strains are known which elaborate an enzyme penicillinase in response to the drug and thus remain insensitive. This led to the development of semi-synthetic penicillins which are not activated by penicillinase, and resistance of staphylococci to these newer penicillins has been reported. However, there is a seemingly never ending demand for anticoccic agents.

A variety of substances are reported which alter host resistance to coccic infections. However, because of the ubiquitous nature of cocci and bacilli, and the diversification of their biological and biochemical characteristics, there is a continuing need for drugs for the treatment of these infections. The existence of multiple antibiotic-resistant strains of the organism suggests the desirability of continuous investigation of drugs for combating the infection. This invention provides an antimicrobial for the treatment of staphylococcic and bacillic infections.

SUMMARY OF THE INVENTION

In accordance with this invention it has been found that selected omega-guanidinoacyl-L-histidines afford desirable degrees of protection against cocci and bacilli infections. In fact these histidine compounds possess an anticoccic activity superior to that of their corresponding omega-guanidino acids.

DETAILED DESCRIPTION OF THE INVENTION

The processes of infection leading to disease are accepted to be a problem in the ecology of the parasite. It is being increasingly realized that the bacterial and host determinants are closely interrelated. Staphylococcal virulence derives from the combined action of several bacterial factors whose effectiveness is conditioned by the reactions of the host. Perhaps the most striking feature of host-parasite relationships in staphylococcal infections is the relatively atypical immunologic response. For this reason additional antimicrobials are always in demand.

By the practice of the invention there is provided an additional method of protecting mammals against bacterial infections. In accordance with the invention an antibacterial amount of certain omega-guanidinoacyl-L-histidines is administered to mammals in need of an antimicrobial effective in protecting against cocci and bacilli. These histidine compounds, administered for the inhibition of bacterial infections, are compounds having the formula (A) $H_2N-C(=NH)-NH-(CH_2)_n-CO-His$ where $n$ is an integer of 1 through 5, i.e. a whole number less than six, and His is histidine, i.e. alpha-amino-4-imidazolepropionic acid. Included are guanidinoacetyl-L-histidine ($n=1$), beta-guanidinopropionyl-L-histidine ($n=2$), gamma-guanidinobutyryl-L-histidine ($n=3$), delta-guanidinovaleryl-L-histidine ($n=4$), and epsilon-guanidinohexanoyl-L-histidine ($n=5$).

The antistaphylococcal activities of the omega-guanidinoacyl-L-histidines will be apparent from the following test results. It has been found the amino acids disappear from the blood stream within six hours after their subcutaneous administration. In the technique employed herein, therefore, a total 5 mg. of each drug was given subcutaneously in equally divided doses two hours before and four hours after the injection of *Staphylococcus aureus*.

The strain of *S. aureus* used in the present investigations and termed "original" strain was isolated from an infected tonsil and has been maintained in our laboratory in the lyophilized state. It is penicillin-resistant, is highly chromogenic, ferments a number of sugars, including mannitol, mannose, maltose, lactose, galactose, glucose, and fructose, and produces coagulase, catalase, gelatinase, deoxyribonuclease, phosphatase, urease, and alpha-toxin.

Culture conditions were standardized, and the third subculture from the lyophilized mother culture was used. The subcultures were grown at 37° C. for 24 hours on Staphylococcus Medium 110 (Difco). The organisms from the third subculture were twice washed and suspended in TC Tyrode Solution (Difco), and the concentration was adjusted turbidimetrically, with a nephelometer, for injection into animals. The transmittance levels on the scale of the instrument were taken as a reference of the density of the suspensions and were correlated with viable bacterial counts. Animals were inoculated subcutaneously with 0.5 ml. of a suspension having 70% transmittance or $2 \times 10^8$ organisms by count. This dosage was approximately 1.5 times the $LD_{50}$.

Swiss albino female mice maintained on the Rockland diet, ranging in age from 8 to 10 weeks and in weight from 20 to 25 grams were used in all tests. All mice were randomized for individual experiments. These mice were propagated in our laboratory from stock originally obtained from Texas Inbred Mice Co., Houston, Texas.

The antistaphylococcal effects of the omega-guanidinoacyl-L-histidine will now be given in tabular form. In the table the compound number is the value of $n$ in formula A given hereinbefore. These are compared with L-Arginine and gamma-aminobutyryl-L-histidine (homocarnosine). Percent protection is (mortality control-mortality treated) × 100/(mortality control) on the fourth day after infection with *Staphylococcus aureus*.

Antistaphylococcal Activity of Omega-guanidinoacyl-L-histidines

| Compound | No. of Animals | Percent Protection Mean | Std. Deviation |
|---|---|---|---|
| 1 | 30 | 45 | 9 |
| 2 | 30 | 58 | 18 |
| 3 | 30 | 78 | 10 |
| 4 | 30 | 65 | 4 |
| 5 | 31 | 71 | 2 |
| Cabu-His* | 72 | 65 | 11 |
| Arginine | 22 | 6 | 5 |

*Gamma-aminobutyryl-L-histidine

The desirable antistaphylococcal activities of the omega-guanidinoacyl-L-histidines of this invention are apparent from the table. Gamma-guanidinobutyryl-L-histidine and epsilon-guanidinohexanoyl-L-histidine afforded unexpectedly high protection, exhibiting an antistaphylococcal activity even greater than homocarnosine. Moreover, as can be seen from the following the omega-guanidinoacyl-L-histidines were generally more potent than their corresponding omega-guanidino acids, and always more potent than their corresponding omega-amino acids.

Comparisons of Guanidino-histidines with Guanidino Acids and Amino Acids

| Compound | Percent Protection on 4th Day Mean |
|---|---|
| Histidine (n = 1) | 45 |
| Glycine | 12 |
| Guanidinoacetic Acid | 50 |
| Histidine (n = 2) | 58 |
| Beta-Alanine | 12 |
| beta-Guanidinopropionic Acid | 32 |
| Histidine (n = 3) | 78 |
| Gaba | 32 |
| gamma-Guanidinobutyric Acid | 44 |
| Histidine (n = 4) | 65 |
| Dava | 51 |
| delta-Guanidinovaleric Acid | 66 |
| Histidine (n = 5) | 71 |
| Eaha | 33 |
| epsilon-Guanidinohexanoic Acid | 57 |

Histidines are those of formula A having $n$ values given in the table; Gaba, gamma-aminobutyric acid; Dava, delta-aminovaleric acid; Eaha, epsilon-aminohexonioc acid. The amino and guanidino acids were available commercially in part. Others were synthesized. The ω-guanidinoacyl-L-histidines were prepared by treating the corresponding ω-aminoacyl-L-histidines with S-ethylisothiourea by the following procedure which is a modification of the one described by Takahashi et al. in Japanese Pat. No. 20564 (*Chem. Abstr.* 60, 2786h (1964)).

EXAMPLE 1

Guanidinoacetyl-L-histidine.$H_2O$ ($n$=1) was prepared from glycyl-L-histidine and S-ethylisothiourea.$H_2SO_4$. Solutions of 1.50 g. of S-ethylisothiourea.$H_2SO_4$ in 5 ml of $H_2O$ and 1.74 g. of Gly-His.HCl in 3 ml of $H_2O$ were adjusted to pH 8–9 with 4 N NaOH. They were then mixed and kept at room temperature for a week. The cloudy suspension was filtered and the filtrate concentrated to dryness in vacuo. The residue, after addition of a small amount of EtOH, was dried in vacuo. A small amount of $H_2O$ was added to dissolve the dry residue and resulting solution was poured onto the column (2.5 cm i.d. × 30 cm Amberlite CG-120, 200–400 mesh, pyridine form). $H_2O$, 1.0 M pyridine, 2.0 M pyridine, and 1.0 M pyridine—0.5 M $NH_4OH$ were used as the effluent solutions. Each fraction was tested for ninhydrin, Pauli, and Sakaguchi reactions. The fractions containing guanidinoacetyl-L-histidine were pooled and concentrated to dryness in vacuo. Cryst from $H_2O$—EtOH; yield, 69.2%; mp, 108–111° C., decomp. Hydrolysis (6 N HCl, 110°, 24 hours.) gave guanidinoacetic acid and histidine, as confirmed be tlc. (thin layer chromatography).

EXAMPLE 2

To prepare beta-guanidinopropionyl-L-histidine.$H_2O$, ($n$=2) S-ethylisothiourea.$H_2SO_4$ (5.0 g) and βAla-His (5.3 g) were reacted by the procedure described in Example 1: yield, 38.8%; mp, 121°–124° C., decomp. Hydrolysis as described in Example 1 gave beta-guanidinopropionic acid and histidine tlc.

EXAMPLE 3

γ-Guanidinobutyryl-L-histidine.$H_2SO_4$ ($n$=3) — S-Ethylisothiourea.$H_2SO_4$ (10.0 g.) and γAbu-His (11.0 g.) were treated as described in Example 1 except for the following changes. For the final crystn, the aq solution was adjusted to pH 5 with 2 N $H_2SO_4$ and abs EtOH was added to form fine white cryst; yield, 51.7%; mp, 119°–124° C., decomp. Hydrolysis as described yielded γ-guanidinobutyric acid and histidine (tlc).

EXAMPLE 4

δ-Guanidino-L-histidine.$H_2SO_4$.$H_2O$ ($n$=4) — S-Ethylisothiourea.$H_2SO_4$ (0.8 g.) and δAvl-His (1.0 g.) were treated in the same way as Example 3; yield, 50.6%; mp, 80°–82° C., decomp. Hydrolysis as above yielded δ-guanidinovaleric acid and histidine (tlc).

EXAMPLE 5

ε-Guanidinohexanoyl-L-histidine ($n$=5) — S-Ethylisothiourea. $H_2SO_4$ (1.4 g.) and εAhx-His (1.7 g.) were treated in the same way as Example 2; yield, 56.1%; mp, 102°–103° C., decomp. Hydrolysis as above gave ε-guanidinohexanoic acid and histidine (tlc).

The yields and physical and analytical data for the compounds prepared in examples 1 through 5 are given in the following table.

ω-Guanidinoacyl-L-histidines

| Compound | Yield, %[a] | Mp, °C[b] | Solvents | Formula | Anal[c] | Color Reaction[d] P | S | N |
|---|---|---|---|---|---|---|---|---|
| n = 1[e] | 69.2 | 108–111 dec | $H_2O$-EtOH | $C_9H_{14}N_6O_3 \cdot H_2O$ | C,H,N | + | + | − |
| n = 2[f] | 38.8 | 121–124 dec | $H_2O$-EtOH | $C_{10}H_{16}N_6O_3 \cdot H_2O$ | C,H,N | + | + | − |
| n = 3[g] | 51.7 | 119–124 dec | $H_2O$-EtOH[h] | $C_{11}H_{18}N_6O_3 \cdot H_2SO_4$ | C,H,N,S | + | + | − |
| n = 4[i] | 50.6 | 80–82 dec | $H_2O$-EtOH[h] | $C_{12}H_{20}N_6O_3 \cdot H_2SO_4 \cdot H_2O$ | C,H,N,S | + | + | − |

-continued

ω-Guanidinoacyl-L-histidines

| Compound | Yield, %[a] | Mp, °C[b] | Solvents | Formula | Anal[c] | Color Reaction[d] P | S | N |
|---|---|---|---|---|---|---|---|---|
| n = 5[j] | 56.1 | 102–103 dec | H₂O-EtOH | $C_{13}H_{22}N_6O_3$ | C,H,N | + | + | − |

[a]Based on ω-aminoacyl-L-histidines.
[b]Melting points were determined by the capilary tube method and were uncorrected.
[c]Analytical results for C,H,N,S were within ±0.4% of the theoretical value.
[d]P, S, and N indicate Pauli, Sakaguchi, and ninhydrin reactions, respectively.
[e]Ir peaks (cm⁻¹) were 620, 660, 818, 935, 984, 1090, 1105, 1190, 1268, 1332, 1398, 1441.
[f]Ir peaks (cm⁻¹) were 618, 661, 935, 986, 1086, 1102, 1181, 1250, 1322, 1393, 1431.
[g]Ir peaks (cm⁻¹) were 620, 808, 918, 990, 1127, 1266, 1398, 1440.
[h]At pH 5.0 (2 N H₂SO₄).
[i]Ir peaks (cm⁻¹) were 615, 820, 918, 980, 1045, 1114, 1256, 1391, 1435.
[j]Ir peaks (cm⁻¹) were 670, 808, 930, 980, 1043, 1082, 1100, 1176, 1260, 1320, 1400, 1430.

The compositions of this invention thus constitute significant new antimicrobials. It is contemplated that they will be taken during periods were contact with staphylococci, streptococci or *Salmonella typhi* infections are likely, such as on entering and during a hospital exposure to the infection. The guanidinoacyl-L-histidine can be taken orally in 250 and 500 mg. tablets or as injections of, say, 150 to 500 mg. The ω-guanidinoacyl-L-histidine per se or combined with an aqueous, vegetable oil, monoglyceride or diglyceride vehicle for injection can be administered, sodium chloride being used if necessary to render the solution isotonic. The solution will contain 0.1 to 15 percent by weight, of the ω-guanidinoacyl-L-histidine.

In the case of tablets, the ω-guanidinoacyl-L-histidine can be combined with suitable colorants, adhesives, and lubricants, along with a solid pharmaceutical diluent, for instance, starches, lactose, sucrose, and other pharmaceutical diluents. These tablets will contain 0.08 percent to 5 weight percent of the ω-guanidinoacyl-L-histidine, preferably 0.08 percent to 1.3 weight percent. Capsules can also be made.

A process is thus provided for the control of infections in humans and other mammals due to cocci and bacilli, which involves administering to the mammal suffering from the infection an effective amount of the ω-guanidinoacyl-L-histidine. In addition other variations and modifications will occur to those skilled in the art. Such ramifications are deemed to be within the scope of this invention.

What is claimed is:

1. A method of protecting a mammal against coccic and bacillic infections which comprises administering to a mammal in need of such protection a bacteria inhibiting amount of an omega-guanidinoacyl-L-histidine having the formula H₂N—C(=NH)—NH—(CH₂)ₙ—CO—Histidine where $n$ is a whole number 1 to 5.

2. The method of claim 1 where $n$ is 1, the histidine compound being guanidinoacetyl-L-histidine.

3. The method of claim 1 where $n$ is 2, the histidine compound being beta-guanidinopropionyl-L-histidine.

4. The method of claim 1 where $n$ is 3, the histidine compound being gamma-guanidinobutyrl-L-histidine.

5. The method of claim 1 where $n$ is 4, the histidine compound being delta-guanidinovaleryl-L-histidine.

6. The method of claim 1 where $n$ is 5, the histidine compound being epsilon-guanidinohexanoyl-L-histidine.

7. An omega-guanidinoacyl-L-histidine having the formula H₂N—C(=NH)—NH—(CH₂)ₙCO—histidine where $n$ is a whole number of 1 to 5.

8. The histidine guanidinoacetyl-L-histidine.

9. The histidine beta-guanidinopropionyl-L-histidine.

10. The histidine gamma-guanidinobutyryl-L-histidine.

11. The histidine delta-guanidinovaleryl-L-histidine.

12. The histidine epsilon-guanididnohexanoyl-L-histidine.

* * * * *